United States Patent
Piver et al.

(10) Patent No.: US 6,620,779 B2
(45) Date of Patent: Sep. 16, 2003

(54) METHOD OF ENHANCING THE EFFICACY OF ANTI-TUMOR AGENTS

(75) Inventors: M. Steven Piver, Buffalo, NY (US); David F. Silver, Buffalo, NY (US)

(73) Assignee: Health Research Inc., Buffalo, NY (US)

( * ) Notice: Subject to any disclaimer, the term of this patent is extended or adjusted under 35 U.S.C. 154(b) by 0 days.

(21) Appl. No.: 10/206,533

(22) Filed: Jul. 26, 2002

(65) Prior Publication Data

US 2002/0198153 A1 Dec. 26, 2002

Related U.S. Application Data

(62) Division of application No. 09/740,501, filed on Dec. 19, 2000, now Pat. No. 6,426,094, which is a continuation of application No. 09/300,124, filed on Apr. 27, 1999, now Pat. No. 6,171,620.

(51) Int. Cl.$^7$ .......................... A61K 37/00; A61K 31/28
(52) U.S. Cl. ................. 514/2; 514/21; 514/12; 514/492
(58) Field of Search ................. 514/2, 21, 12, 514/492

(56) References Cited

U.S. PATENT DOCUMENTS 5,922,674 A    7/1999    Anagnostou et al.

FOREIGN PATENT DOCUMENTS

JP    02096535    4/1990

OTHER PUBLICATIONS

Cascinu et al., Oncology Reports, (1994), vol. 1, No. 1, pp. 169–172 Abstract Only.*
Huinink, et al. Further Studies to Ameliorate Toxicity of Carboplatin. Seminars in Oncology, Apr. 1994, vol. 21, No. 2, Suppl. 2, pp. 27–33.
Abels. Use of Recombinant Human Erythropoietin in the Treatment of Anemia in Patients Who Have Cancer. Seminars in Oncology, Jun. 1992, vol. 19, No. 3, Suppl. 8, pp. 29–35.
Wood, et al., Cisplatin–associated Anemia: An Erythropoietin Deficiency Syndrome: Journal of Clinical Investigation, Inc. Apr. 1995, vol. 95, pp. 1650–1659.
Database CAPLUS on STN (Columbus, OH, USA), Accession No. 1998:84493. Baldwin, et al. Erythropoietin Ameliorates Anemia of Cisplatin Induced Acute Renal Failure. Abstract, ASAIO J. 1998, vol. 44, No. 1, pp. 44–47.
Database CAPLUS on STN (Columbus, OH, USA), Accession No. 1991:224638. Masunaga, et al. Effects of Recombinant Human Erythropoietin (SND–5001) on Renal Anemic Rats Induced by Drugs. Abstract, Nippon Yakurigaku Zasshi 1991, vol. 98, No. 2, pp. 151–160.
Database CAPLUS on STN (Columbus, OH, USA), Matsumoto, et al. Effects of Recombinant Human Erythropoietin on Anticancer Drug–induced Anemia. Abstract, Br. J. Haematol, 1990, vol. 75, No. 4, pp. 463–468.

* cited by examiner

*Primary Examiner*—Jerome D. Goldberg
(74) *Attorney, Agent, or Firm*—Hodgson Russ LLP

(57) ABSTRACT

A method for enhancing the effect of anti-tumor agents on solid tumors is provided. The method comprises administering to an individual an anti-tumor agent and a hematocrit elevator. The hematocrit elevator may be administered before or concurrently with the anti-tumor agent.

4 Claims, 2 Drawing Sheets

METHOD OF ENHANCING THE EFFICACY OF ANTI-TUMOR AGENTS

This-application is a divisional of U.S. patent application Ser. No. 09/740,501, filed on Dec. 19, 2000, now U.S. Pat. No. 6,426,094, which is a continuation of U.S. patent application Ser. No. 09/300,124 filed on Apr. 27, 1999, now U.S. Pat. No. 6,171,620, the disclosures of which are incorporated herein by reference.

FIELD OF THE INVENTION

This invention relates to the field of treatment of cancer. More particularly, this invention, relates to increasing the efficacy of chemotherapeutic agents for the treatment of solid tumors by improving the hematocrit during chemotherapy.

BACKGROUND OF THE INVENTION

Anti-Tumor Agents

While numerous advances have been made in the treatment of cancer, solid tumors remain difficult to treat. Consequently, many patients develop advanced cancer for which conventional therapies are generally not effective. As a result, novel types of cancer drugs are being investigated for anti-cancer activities. In recent years, considerable interest has been generated in platinum coordination compounds (Rosenberg et al., 1969, Nature, 222:385–386). Structurally, they represent a complex formed by a central atom of platinum and surrounded by various arrangements of chlorine atoms and ammonia groups in either a cis or trans relationship. Platinum-based multiagent chemotherapy has become the first line post-surgical therapy for patients with advanced ovarian cancer (American Cancer Society, 1995, Facts and Figures). Cisplatin (cis-diamine dichloro platinum) and Carboplatin (1,1,-cyclobutanedicarboxyl diammine platinum-(II)) are examples of cytotoxic platinum coordination compounds that are useful for treatment of a variety of malignancies. Other platinum compounds known to exhibit cytotoxic effects towards cancer cells include 1,4, and 1,2-diaminocyclohexane platinum(IV) complexes (U.S. Pat. No. 5,434,256).

Although, platinum compounds are useful against malignancies, the development of tumor resistance during the course of treatment limits their usefulness. Many of the specific antitumor mechanisms of platinum are not fully understood. Without detailed mechanistic information of platinum cytotoxicity, it has been difficult to overcome the problem of tumor resistance to cisplatin and therefore to enhance the efficacy of platinum and other anti-tumor agents.

Solid tumors contain populations of both well-oxygenated cells and hypoxic cells. Hypoxia usually occurs in cells that are farthest from the blood supply. Such cells proliferate slowly but are also relatively resistant to anti-cancer drugs. For example, data suggests that the cytotoxic effects of cisplatin are met with greater resistance by hypoxic tumor cells than by oxygenated cells (Herman et al., 1988, Cancer Research, 48:2342–2347; Melvic et al., 1988, Radiat. Res., 114:489–499; Grau et al., 1988, Radiother. Oncol., 13:301–309). Thus, one mechanism by which tumors display resistance to anti-cancer agents may be attributable to their relatively hypoxic state.

Some commonly observed side effects like renal toxicity, ototoxicity, and nephrotoxicity limit the efficacy of platinum compounds. Anemia is also a common side effect of platinum therapy. Anemia is especially common following cisplatin therapy, and patients often require blood transfusions. Although the cause of anemia following cisplatin therapy may be multifold, erythropoietin levels are found to be reduced and therefore, erythropoietin deficiency appears to be important. Recombinant human erythropoietin administered following cisplatin therapy or other chemotherapy has been reported to be effective in reversing anemia associated with such therapy (Abels 1992, Seminars in Oncology, 19:29–35).

Erythropoiesis Regulators

The existence of a hormone that regulates erythropoiesis, the production of red blood cells, was first proposed at the beginning of the century. Since then, data has continued to mount in favor of humoral regulation of erythropoiesis. This led to the purification of erythropoietin (EPO) and determination of its amino acid sequence and ultimately to the cloning of the human EPO gene (Jacobs et al., 1985, Nature, 313:806–810; Lin, 1985, Proc. Natl. Acad. Sci., 82:7580–7584; Lin, U.S. Pat. No. 4,403,008). Purification of recombinant EPO is described in U.S. Pat. No. 4,667,016 to Lai et al.

EPO is a hormone essential in regulating levels of red blood cells in circulation. Naturally occurring EPO is produced by liver during fetal life and mainly by kidneys in adults. Recombinant erythropoietin produced by genetic engineering techniques involves the expression of a protein product from a host cell transformed with the gene encoding erythropoietin. Similar to many cell surface and secretory proteins, EPO is glycosylated. Glycosylation is usually of two types: O-linked oligosaccharides are attached to serine or threonine residues while N-linked oligosaccharides are attached to asparagine residues. Human urinary derived erythropoietin contains three N-linked and one O-linked oligosaccharides chains which comprise about 40% of the total molecular weight of the glycoprotein. Different isoforms of erythropoietin corresponding to various glycosylation levels have been described (Elliott et al., 1995, EP 0640619A1).

Erythropoietin exerts its effect by binding to the erythropoietin receptor. Activation of the EPO receptor results in several biological effects including stimulation of proliferation, stimulation of differentiation and inhibition of apoptosis (Liboi et al., 1993, Proc. Natl. Acad. Sci., USA, 1990, 11351). EPO receptor can also be activated by agonists like EPO mutants and analogs, peptides, and antibodies. In addition to EPO, other compounds with erythropoietin-like activity have also been identified. For example, a molecule identified from a renal cell carcinoma has been reported to have an EPO-like effect on erythropoiesis but is immunologically distinct from EPO (Sytkowski et al. 1979). Other stimulators of erythropoiesis include water soluble salts of transition metals (Brugnara et al., U.S. Pat. No. 5,369,014).

While platinum therapy is becoming more acceptable for advanced solid tumors, clinical correlates between hematocrit or hemoglobin and the anti-tumor effect of chemotherapeutic agents has not been evaluated to determine if agents that enhance hematocrit increase the sensitivity of tumors to anti-cancer agents. Given the increasing use of non-conventional anti-cancer agents, there is a continuing need to enhance the antitumor response to these agents.

SUMMARY OF THE INVENTION

The present invention discloses a method for enhancing the efficacy of anti-tumor agents. The method comprises administering to an individual, in need of such a treatment, an anti-tumor agent under conditions of elevated hematocrit.

Thus, an object of the present invention is to provide a method for the treatment of solid tumors by administration of a combination of an anti-tumor agent and a hematocrit elevator. In a preferred embodiment, the hematocrit elevator is administered prior to the anti-tumor agent.

Another object of the present invention is to provide a method for the treatment of solid tumors by administration of an anti-tumor platinum compound and erythropoietin or an erythropoietin like compound.

A further object of the present invention is to provide a method of treatment of ovarian tumors by administration of a combination of cisplatin and erythropoietin.

DETAILED DESCRIPTION OF THE INVENTION

Figure 1:
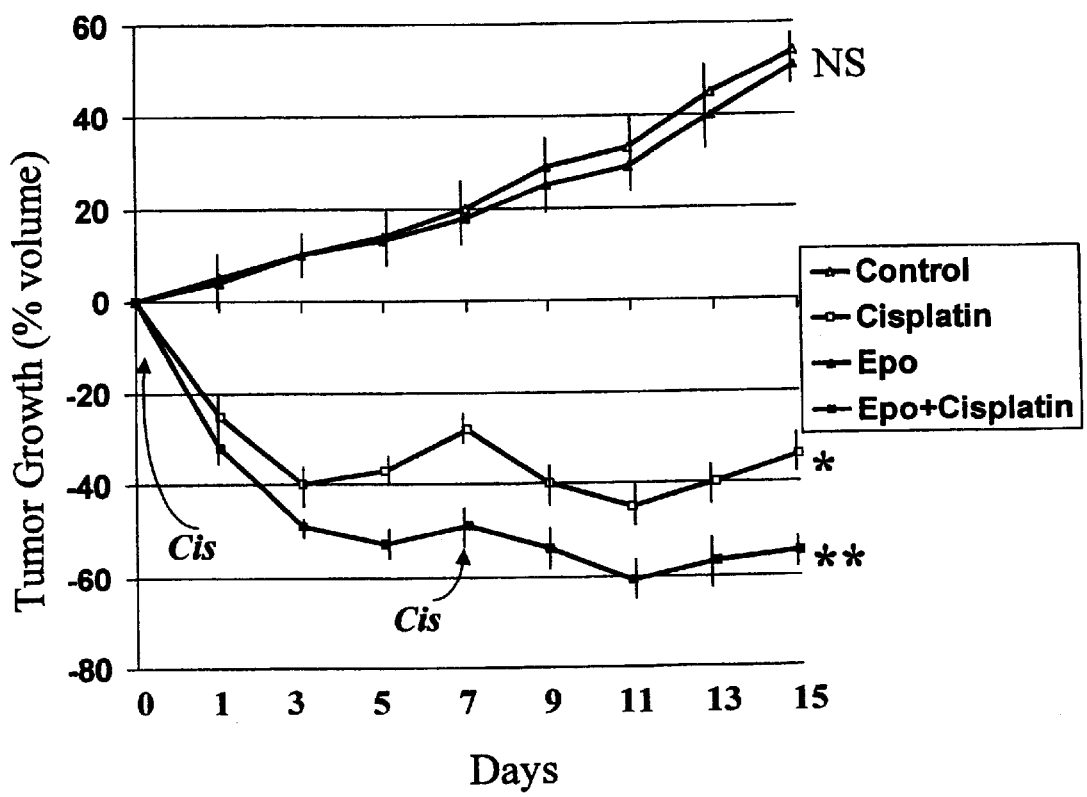
FIG. 1 is a representation of the effect of administration of cisplatin, erythropoietin, or both on ovarian tumor growth as a function of time.

By the term "malonato platinum coordination compound (s)" as used herein for the purposes of specification and claims is meant, cis and trans isomers of platinum(II) and platinum(IV) which contain the bidentate malonato bidentate ligand which may be substituted or unsubstituted. Platinum II forms coordination compounds which have a planar arrangement in space while platinum IV forms coordination compounds which have an octahedral arrangement in space. Such compounds are disclosed in U.S. Pat. No. 4,140,707 and 4,657,927 to Cleary et al., which are herein incorporated by reference.

The terms "anti-tumor agent" and "anti-cancer agent" are used interchangeably and for the purposes of specification and claims mean, a compound or composition effective in inhibiting, slowing, or arresting the growth of cancerous cells, or which exhibit cytotoxic effects on cancerous cells. By the term "chemotherapeutically effective amount" of an anti-tumor agent is meant for the purposes of specification and claims, an amount administered to an individual sufficient to cause inhibition, slowing or arresting of the growth of cancerous cells, or which is sufficient to produce cytotoxic effect on cancerous cells.

By the term "anti-tumor effect" or "anti-tumor activity" is meant for the purposes of specification and claims, the inhibition, slowing or arrest of the growth of cancerous cells, or the exhibition of cytotoxic effect. An example of a measurable anti-tumor effect is the reduction in the size of a tumor.

By the term "Erythropoietin" or "EPO" is meant for the purposes of specification and claims, erythropoietin in whole or in part obtained or isolated by chemical isolation, and purification techniques; and erythropoietin of any type including human, manufactured by using recombinant DNA techniques. This term also includes erythropoietin produced by the cells of the individual due to transfection with exogenous genetic material comprising the gene encoding EPO, or due to implantation of transfected primary or secondary cells containing exogenous genetic material comprising the gene encoding EPO into such individual. The techniques for production and delivery of the product or transfected cells are disclosed in U.S. Pat. No. 5,733,761 which method is herein incorporated by reference.

By the term "Erythropoietin-like" molecule or substance is meant for the purposes of specification and claims, any molecule obtained by chemical isolation and purification techniques or by recombinant techniques that has the ability to activate the erythropoietin receptor or otherwise mimic the actions of erythropoietin, such as stimulation of erythropoiesis. Thus, this definition includes a fragment of native or recombinant EPO, which may be shorter in length than the entire EPO molecule and can activate the EPO receptor; a fused molecule, comprising in part, amino acid sequences normally present in the intact EPO molecule; an analog, such as those disclosed in U.S. Pat. No. 5,888,772 to Okasinski, incorporated herein by reference, whose amino acid sequence is similar to, but not identical to, the naturally occurring EPO and which has the biological activity of stimulating erythropoiesis; EPO derivatives, in which the EPO structure has been modified by the addition (or deletion) of one or more substituents or chemical moieties; isoforms of EPO which include the various glycosylation states of EPO, for example as described by Strickland in U.S. Patent No, 5,856,298, incorporated herein by reference; recombinantly produced isoforms of EPO containing additional glycosylation sites or rearranged glycosylation sites as disclosed in European Patent to Eliott et al. (EP 0640619B1), incorporated herein by reference; peptides, such as those disclosed in U.S. Pat. No. 5,773,569 to Wrighton et al., and U.S. Pat. No. 5,835,382 to Wilson et al., incorporated herein by reference, that bind to and activate the EPO receptor or otherwise behave as EPO agonists ; mutated secretable EPO proteins, such as those disclosed in U.S. Pat. No. 5,614,184 to Sytkowski et al., incorporated herein by reference, which have altered biological activity. Also included in this definition are agonistic antibodies or fragments thereof, such as disclosed in U.S. Pat. No. 5,885, 574 to Elliott et al., incorporated herein by reference. which activate erythropoietin receptor or otherwise mimic the actions of EPO. A common feature of all of the erythropoietin-like substances is the ability to mimic one or more actions of EPO.

By the term "therapeutically effective" amount of hematocrit elevator is meant an amount of naturally derived or recombinantly produced EPO or EPO-like substance sufficient to improve the production of red blood cells thereby increasing the hematocrit above normal range. For example, an amount in the range of 15 to 1,500 units per kg body weight, preferably 50–300 units/kg is disclosed as therapeutically effective in U.S. Pat. No. 5,013,718, which disclosure is herein incorporated by reference.

The present invention relates to a method for enhancing the effect of certain anti-tumor agents by improving the hematocrit. The method of the present invention comprises the steps of administering to a patient in need of such a treatment, a combination of an anti-tumor agent and an agent that increases the hematocrit.

The methods of the present invention are useful for treatment of mammalian cancer tumors including human cancer tumors, particularly, solid tumors that are susceptible to treatment with platinum compounds. Examples of such tumors include, but are not limited to, adenocarcinomas, melanomas, lymphomas, sarcomas, and lung, breast, ovarian, head and/or neck, prostate, cervical, endometrial, colorectal, gastric, liver, fallopian tubes, esophagus, small intestine, pancreas, kidney, adrenal, vaginal, vulvar, brain and testicular tumors.

For the method of the present invention, one or more anti-tumor agents are administered in combination with an agent which increases the hematocrit. The anti-tumor agent and the hematocrit elevator may be administered concurrently or sequentially. Preferably, the hematocrit elevator is administered before the anti-tumor agent. An example of an anti-tumor agent is a platinum containing compound such as any of the platinum coordination compounds. The platinum coordination compounds of the present invention include, but are not limited to, platinum(II) and platinum (IV) compounds.

Two examples of platinum compounds that are known to have cytotoxic effects on cancer cells are cisplatin and carboplatin. These two compounds belong to a group of compounds known as "malonato" due to the presence in their structure of $(OOC)_2$-C linkage. Cisplatin is a yellowish white powder and contains chlorine and ammonia groups in a horizontal plane. Carboplatin is a white to off white crystalline powder. Like cisplatin, carboplatin has been used to treat a variety of human cancers, including small cell lung cancer, squamous cell carcinomas, and testicular cancer (see U.S. Pharmacists, September, 1989, pages 62–63). While not intending to be bound by any theory, it is believed that the platinum coordination compounds exert anti-tumor activity by interfering with DNA synthesis by causing cross-linking of complementary strands of DNA. In a preferred embodiment, the platinum compound is cisplatin.

The anti-tumor agent is administered to a patient in a pharmaceutically acceptable carrier by conventional routes appropriate for the particular chemotherapy. For example the anti-tumor agent may be delivered by intravenous, intraperitoneal, subcutaneous, intramuscular routes, or by infusion to ensure its delivery into the bloodstream in an effective form. In addition, the anti-tumor agents may be administered in liposomal encapsulations as disclosed in U.S. Pat. No. 5,620,703, incorporated herein by reference. Effective doses of anti-tumor agents for the present invention are those which are known to have an anti-tumor effect. Such doses are known to those skilled in the art or can be determined empirically. For example, guiding principles for dosage of many chemotherapeutics are generally set out in the Physician's desk Reference. Typically, the dosage of platinum compound ranges from about 1 to about 200 mg/kg/dose. These compounds may be administered as a single infusion or as multiple infusions over a period of days, e.g., 3–5 days. The cycle may be repeated as needed. Preferably it is administered with a single intravenous injection on day 1 of the treatment. The dosage of cisplatin is generally in the range of 25–300 mg/m$^2$. A more preferable range is 50–100 mg/m$^2$. To maintain sufficient hydration, normal saline is administered prior to and following cisplatin infusion.

The hematocrit elevators of the present invention include any agent which will increase the number of red blood cells in the individual being treated with the agent. For example, hematocrit elevators useful for the method of the present invention include, but are not limited to, erythropoietin and erythropoietin-like substances. The hematocrit elevators may be administered by conventional means including, but not limited to intravenous, intraperitoneal or subcutaneous routes, in doses that are known to those skilled in the art to be useful for the purposes of increasing the hematocrit. EPO may be administered in multiple doses based on its half life in the plasma of about 5 hours. Alternatively, transfection techniques may also be used to deliver EPO to the cells of the individual. Hematocrit values can be monitored as an indicator of the effectiveness of EPO. Similar administration routes can be used for EPO-like substances. In a preferred embodiment, 50–100 units/kg body weight is administered three times per week by intravenous or subcutaneous routes.

The effectiveness of the treatment can be determined by evaluating tumors. Palpable tumors can be measured by conventional means. Imaging techniques such as CT scan, MRI scan, ultrasonography and the like can also be used to measure and evaluate tumor size. Alternatively, specific tumor markers such as, but not limited to, PSA for prostate cancer, CA-125 for ovarian cancer, CA-15-3 for breast cancer can also be quantitated for providing tumor evaluations. Standard criteria can be used to evaluate response. For example the criteria set forth in the WHO handbook of Reporting Results of Cancer Treatment, WHO Offset Publication 1979, may be followed. Thus, tumors may be classified as Complete response, Partial response or No-response. The treatment cycles of cisplatin and EPO may be continued until an acceptable response is achieved or until unacceptable toxic effects are observed.

EXAMPLE 1

This embodiment demonstrates a cisplatin-sensitizing effect on human cells engrafted in SCID mice induced by the pretreatment, elevation and maintenance of the hematocrit using EPO. To illustrate this embodiment, experiments were carried out in immunodeficient SCID mice bearing human ovarian cancer. Such mice are recognized by those skilled in the art as suitable animal models for the demonstration of anti-tumor activities of potential chemotherapeutic agents.

Eighty CB 17-SCID/SCID mice (Taconic Labs) were used. The animals were kept under sterile and light-controlled conditions. Portions of tumors from patients with recurrent stage IIIC, grade 3, papillary serous adenocarcinoma of the ovary were implanted and propagated in SCID mice by procedures well known to those skilled in the art. Briefly, xenografts were grown and passaged at least five times prior to the implantation of tumors into experimental animals. In 40 experimental mice at six weeks of age, 2–3 mm portions of the human xenograftic tumors were implanted by suture ligation to the gonadal fat pad (GFP) according to the method described by Sakakibara et al. (1996, Can. J. Sci. Amer., 2:291–300), which method is incorporated herein by reference. The GFP tumor xenografts grew to large intraperitoneal masses palpable by abdominal examination. Each mouse subsequently underwent a laparotomy via a midline incision extending from the sternum to the level of the iliac crests. Adhesions to the tumor were lysed and the tumor was lifted out of the peritoneal cavity without violating the GFP pedical. Tumor measurements were taken in three dimension with vernier calipers. The tumor was then placed back in its original intraperitoneal location followed by single layer closure of the abdomen. Three days post operatively, the treatment protocols were initiated. Mice were randomly selected to be placed in one of four treatment groups. Day zero was defined as the first day of intraperitoneal (ip) cisplatin or ip phosphate buffered saline (PBS) injections. Group I animals (controls) received 100 µl of PBS three times per week subcutaneously from day −15 to day +6 and 300 µl PBS ip on day 0. Mice in Group II (EPO group) received EPO subcutaneously at a dose of 20 units in 100 µl of PBS three times per week from day −15 to day +6 and 300 µl of PBS ip on day 0. Mice in Group III (cisplatin group) received cisplatin ip at a dose of 5 mg/kg in 300 µl of PBS on day 0 and 100 µl of subcutaneous PBS three times per week from day −15 to day +6. Mice in Group IV (EPO+cisplatin group) received subcutaneous EPO injections as in Group II from day −15 to day +6 and ip cisplatin injections as in Group III on day 0. Mice were observed until day 8.

Automated hematocrits were obtained from tail bleeds performed on three mice selected randomly from each group on days −15, −7, 0, and +7. No mouse was bled twice. On day 7, mice were sacrificed and necropsies were performed. Tumors were excised and measured in three dimensions with vernier calipers. Tumor volume was calculated as follows.

(Width)×(Length)×(Depth)=Tumor Volume

The percent growth of the tumor was calculated using the formula:

[(Necropsy Tumor Volume/Initial Tumor Volume)−1]×100=Percent Tumor Growth

The size of the tumors on initial laparotomy was approximately 2 cm×1.5 cm×1 cm in three dimensions and was the same in each treatment group. A significant difference in the tumor growth was observed in the groups treated with and without cisplatin. A difference (P=0.07), suggestive of an enhancement in the effect of cisplatin by EPO, was observed between the tumor size of mice that received cisplatin alone and mice that received cisplatin plus EPO. No difference was observed between the controls and the EPO group.

In another illustration of this embodiment, cisplatin was administered twice during the treatment. In additional forty experimental mice at six weeks of age, 2 mm portions of human ovarian cancer xenografts were implanted. Treatment groups were randomly assigned three days after implantation. Group I animals (controls) received 100 µl of PBS three times per week subcutaneously from day −15 to day +13 and 300 µl PBS ip on day 0 and 7. Mice in Group II (EPO group) received EPO subcutaneously at a dose of 20 units in 100 µl of PBS three times per week from day −15 to day +13 and 300 µl of PBS ip on day 0 and 7. Mice in Group III (cisplatin group) received cisplatin ip at a dose of 5 mg/kg in 300 µl of PBS on day 0 and 7, and 100 µl of subcutaneous PBS three times per week from day −15 to day +13. Mice in Group IV (EPO+cisplatin group) received subcutaneous EPO injections as in group 2 three times per week from day −15 to day +13 and ip cisplatin injections as in group 3 on day 0 and 7. Mice were observed until day +15.

Automated hematocrits were obtained as described above on days −15, −7, 0, +7, and +14. The change in hematocrit relative to the initial hematocrit was plotted over time. Serial measurements of tumor nodules were made in two dimensions using vernier calipers starting on day zero. On day zero, tumors had grown to approximately 4 mm×5 mm in size in each group. Tumor volumes were calculated on days 0, +1, +3, +5, +7, +9, +11, +13 and +15 using the formula.

(Length)×(Width)$^2$/2=Tumor volume

Percent tumor growth was calculated for each index day compared to day 0 and plotted over time. Statistical analysis included Student T tests for the overall tumor growth in the large GFP tumor experiment. The growth curves developed in the smaller subcutaneous tumor group and the curves representing change in the hematocrit over time were analyzed by analysis of variance. Significance was defined by P values less than 0.05.

When cisplatin was administered twice a week, a significant difference was observed (p<0.05) between the EPO+cisplatin group and the cisplatin group (FIG. 1). Tumor growth curves plotted for the mice bearing subcutaneous tumor nodules demonstrated significantly more tumor regression in the EPO plus cisplatin group compared to the cisplatin group. Again, no difference was observed between the controls and the EPO group.

Figure 2:
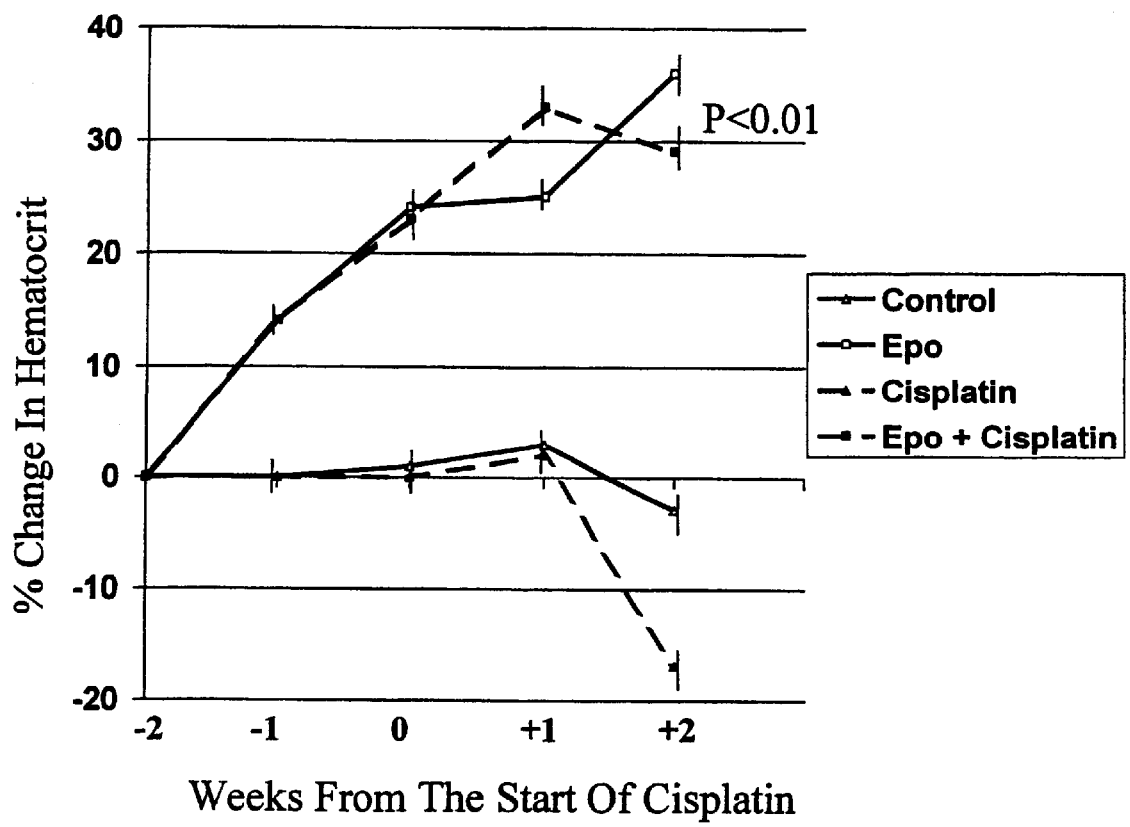
FIG. 2 is a representation of the effect of administration of cisplatin, erythropoietin, or both on the percent change in hematocrit as a function of time.

Weekly hematocrits and the percent change in the hematocrits over time for the mice bearing small subcutaneous tumors are represented in Table 1 and FIG. 2 respectively. Hematocrit from mice bearing large GFP tumors were similar (data not shown). The administration of EPO resulted in a 25–35% increase in the hematocrit compared to its initial value (on week −2) and was significantly different than controls (p<0.01). Cisplatin without EPO resulted in a 20% decrease in the hematocrit. Tumor bearing mice in the control group had a 2% decrease in their hematocrit over time (FIG. 2).

TABLE 1

| | Hematocrits | | | |
|---|---|---|---|---|
| Time | CONTROL | EPO | CISPLATIN | EPO + CISPLATIN |
| Week −2 | 39.5 ± 0.1 | 39.5 ± 0.2 | 39.8 ± 0.2 | 39.6 ± 0.2 |
| Week −1 | 39.7 ± 0.3 | 44.9 ± 0.2 | 39.8 ± 0.2 | 45.1 ± 0.3 |
| Week  0 | 39.8 ± 0.3 | 48.9 ± 0.3 | 39.8 ± 0.3 | 48.9 ± 0.2 |
| Week +1 | 40.8 ± 0.2 | 49.3 ± 0.3 | 40.7 ± 0.1 | 52.7 ± 0.3 |
| Week +2 | 38.6 ± 0.3 | 53.6 ± 0.4 | 33.1 ± 0.3 | 50.9 ± 0.3 |

These data demonstrate a significantly greater tumor regression using EPO and cisplatin compared to mice treated with cisplatin alone. Mice in the EPO+cisplatin group had an elevation in their Hematocrits of 25–35% compared to mice in the cisplatin group.

EXAMPLE 2

This embodiment demonstrates that increasing the hematocrit reduces the toxicity related mortalities of anti-tumor agents. To illustrate this embodiment, performance status of mice from Example 1 receiving the various treatments was evaluated. Performance status was assessed on days 0, +7, and +14 using five objective criteria associated with morbidity and mortality in experimental mice. The five criteria were (1) ruffled fur; (2) weakness/lethargy; (3) 20% weight loss compared to the mean weight of control animals; (4) kyphotic hunched posturing; and (5) death. A grade of 0 equaled normal health and a grade of 5+ equaled death.

Performance status scores of all mice on day 0 indicated normal healthy mice in each treatment group (all scores =0). As shown in Table 2, by day +7, signs of morbidity from cisplatin were noted (Table 2). All mice in the control group and the EPO group maintained performance status scores of zero. Among the 10 mice in the cisplatin group, all had ruffled fur, all had signs of weakness/lethargy, and 6 had a 20% weight loss compared to controls on day +7. All mice in the EPO +cisplatin group had ruffled fur and 7 demonstrated signs of weakness/lethargy. On day +14, the performance status of mice in the cisplatin group deteriorated to include 4 mortalities and 3 of the mice had hunched posturing. Only 1 mortality was observed in the EPO +cisplatin group and 1 additional mouse developed hunched posturing (Table 2).

TABLE 2

| MOUSE NO. | CONTROL | EPO | CISPLATIN | EPO + CISPLATIN |
|---|---|---|---|---|
| 1 | 0 | 0 | + + + + + | + + |
| 2 | 0 | 0 | + + + | + + + |
| 3 | 0 | 0 | + + + + | + + + |
| 4 | 0 | 0 | + + + + + | + + |
| 5 | 0 | 0 | + + + + + | + + + |
| 6 | 0 | 0 | + + + | + + + + |
| 7 | 0 | 0 | + + + + | + + |

TABLE 2-continued

| MOUSE NO. | CONTROL | EPO | CISPLATIN | EPO + CISPLATIN |
|---|---|---|---|---|
| 8 | 0 | 0 | +++ | ++ |
| 9 | 0 | 0 | ++++ | +++++ |
| 10 | 0 | 0 | +++++ | +++ |
| Total | 0 | 0 | 43+ | 29+ |

Thus, there was more morbidity observed in the cisplatin treated animals compared to the EPO+cisplatin treated mice. Furthermore, mice treated with EPO maintained a better performance status and had fewer cisplatin-related morbidities. While not intending to be bound by any theory, it is hypothesized that the enhanced anti-tumor effect obtained in the EPO+cisplatin group was due to an increased hematocrit rather than maintenance of an acceptable performance status.

It should be understood that while the invention has been described in detail herein, the examples were for illustrative purposes only. Other modifications of the embodiments of the present invention that are obvious to those skilled in the art are intended to be within the scope of the appended claims.

What is claimed is:

1. A method of improving the efficacy of carboplatin comprising the steps of administering to an individual in need of treatment:
    (a) a chemotherapeutically effective amount of carboplatin; and
    (b) erythropoietin,
wherein the combination of carboplatin and erythropoietin has a synergistic anti-tumor effect.

2. The method of claim 1, wherein the carboplatin is administered in a dose of between 25 mg/m$^2$ to 300 mg/m$^2$.

3. The method of claim 2, wherein the carboplatin is administered in a dose of between 50 mg/m$^2$ to 100 mg/m$^2$.

4. The method of claim 1, wherein the erythropoietin is administered prior to carboplatin.

* * * * *